(12) United States Patent
Kishi et al.

(10) Patent No.: US 8,597,196 B2
(45) Date of Patent: Dec. 3, 2013

(54) CARDIAC SIGNAL PROCESSING APPARATUS AND CARDIAC SIGNAL PROCESSING METHOD

(71) Applicants: Takahiko Kishi, Yokohama (JP); Jun-ichi Takada, Sagamihara (JP); Satoshi Suzuki, Toyonaka (JP); Tomoyoshi Yasue, Toyota (JP)

(72) Inventors: Takahiko Kishi, Yokohama (JP); Jun-ichi Takada, Sagamihara (JP); Satoshi Suzuki, Toyonaka (JP); Tomoyoshi Yasue, Toyota (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 13/729,920

(22) Filed: Dec. 28, 2012

(65) Prior Publication Data
US 2013/0197377 A1 Aug. 1, 2013

(30) Foreign Application Priority Data
Jan. 26, 2012 (JP) ................................ 2012-014429

(51) Int. Cl.
*A61B 5/024* (2006.01)
(52) U.S. Cl.
USPC ......................................................... 600/508
(58) Field of Classification Search
USPC ......................................................... 600/508
See application file for complete search history.

(56) References Cited

U.S. PATENT DOCUMENTS 6,041,250 A * 3/2000 dePinto .......................... 600/509

FOREIGN PATENT DOCUMENTS

JP A-2009-55997 3/2009
JP A-2010-286268 12/2010

OTHER PUBLICATIONS

Lee, S. et al., "Noncontact Vital Sign Detector Based on Miniaturized Radars," *2011 Microwave Workshop & Exhibition*, Nov. 2011.
Xiao, Y. et al., "Accuracy of a Low-Power Ka-Band Non-Contact Heartbeat Detector Measured from Four Sides of a Human Body," *Microwave Symposium Digest 2006*, Jun. 2006, IEEE MTT-S International.

\* cited by examiner

*Primary Examiner* — Michael Kahelin
(74) *Attorney, Agent, or Firm* — Oliff & Berridge, PLC

(57) ABSTRACT

A cardiac signal processing apparatus includes: a unit for acquiring, from a heartbeat sensor, cardiac signals relating to heartbeats of a subject; a low-pass filter for allowing passage of those cardiac signals having a first predetermined frequency or lower, among the cardiac signals; higher harmonic noise acquisition unit for acquiring harmonic signals of low-frequency noise by performing high frequency extrapolation on the signals output from the low-pass filter; a high-pass filter for allowing passage of those cardiac signals having a second predetermined frequency or higher, among the cardiac signals; and higher harmonic noise removal unit for removing the harmonic signals of low-frequency noise from the signals output from the high-pass filter. It is thus made possible to remove noise from the cardiac signals and to obtain desirable heartbeat detection characteristics.

7 Claims, 3 Drawing Sheets

CARDIAC SIGNAL PROCESSING APPARATUS AND CARDIAC SIGNAL PROCESSING METHOD

BACKGROUND OF THE INVENTION

1. Field of the Invention

This invention relates to a cardiac signal processing technique.

2. Description of the Related Art

Known methods of detecting heartbeats of a living body include a method of detecting body surface displacement with use of a piezoelectric sensor, a pneumatic sensor, an electromagnetic wave Doppler sensor, a ultrasonic wave Doppler sensor or the like. Also known is a method of detecting body surface movement occurring in response to beats of the heart by applying microwaves to a region around the chest of a subject to be measured (Patent Literature 1, Non-Patent Literature 1).

When using the method of measuring body surface displacement, the measurement is apt to be affected more significantly by noise caused by extraneous vibration or body motion of the subject himself/herself, because body surface displacement is relatively small. It is reported that when using the method of measuring body surface movement in a region around the chest, a respiratory signal with higher harmonics interfere with a cardiac signal (Non-Patent Literature 2). Non-Patent Literature 2 discloses that in order to suppress such interference, microwaves are transmitted by double side-band, and microwaves are transmitted to the back side of the chest.

PRIOR ART DOCUMENTS

Patent Literatures

Patent Literature 1: Japanese Patent Application Publication No. 2009-055997

Patent Literature 2: Japanese Patent Application Publication No. 2010-286268

Non-Patent Literatures

Non-Patent Literature 1: Sungeun Lee, et. at., "Noncontact Vital Sign Detector Based on Miniaturized Radars", 2011 Microwave Workshop & Exhibition, November 2011.

Non-Patent Literature 2: Yanming Xiao, et. al., "Accuracy of A Low-Power Ka-Band Non-Contact Heartbeat Detector Measured from Four Sides of A Human Body", Microwave Symposium Digest 2006, IEEE MTT-S International, June 2006.

SUMMARY OF THE INVENTION

In Non-Patent Literature 2, as described above, the interference by a respiratory signal with higher harmonics is suppressed by devising a method of detecting a cardiac signal. However, there are various methods of detecting a cardiac signal based on body surface movement around the chest, in any of which the detection is inevitably affected more or less by a respiratory signal with higher harmonics. The technique disclosed in Non-Patent Literature 2 restricts the detection method. If cardiac signal is obtained by any other method, the interference by the respiratory signal with higher harmonics cannot be removed from the cardiac signal.

Furthermore, in an environment where vibration is continuously generated like in a vehicle, or where vibration from music or sound noise is continuously generated, it is also required to remove such noise.

This invention has been made in view of the problems as described above, and an object of the invention is to provide a technique capable of removing noise from a cardiac signal to achieve desirable heartbeat detection characteristics.

A cardiac signal processing apparatus according to the invention has:

a cardiac signal acquisition unit configured to acquire cardiac signals relating to heartbeats of a subject;

a low-pass filter configured to allow passage of those cardiac signals having a first predetermined frequency or lower, among the cardiac signals;

a higher harmonic noise acquisition unit configured to acquire harmonic signals with low-frequency noise by performing high frequency complementation on the signals output from the low-pass filter unit;

a high-pass filter configured to allow passage of those cardiac signals having a second predetermined frequency or higher, among the cardiac signals; and a higher harmonic noise removal unit configured to remove the harmonic signals of low-frequency noise from the signals output from the high-pass filter unit.

Employment of such signal processing makes it possible to remove higher harmonic component of a respiration-derived signal from a cardiac signal. Therefore, no matter what detection method is employed for detecting a cardiac signal, it is made possible to remove interference by respiratory harmonics when the respiratory harmonics interfere with a cardiac signal, and desirable heartbeat detection characteristics can be achieved.

In the invention, the cardiac signal may be a signal obtained by measurement based on displacement on a body surface around the chest or displacement in the body of the subject. Displacement on the body surface can be obtained, for example, based on reflected waves of electromagnetic waves or supersonic waves applied to the body surface of the subject, or can be obtained with use of a piezoelectric sensor or a pneumatic sensor. Displacement in the body can be obtained, for example, based on transmitted waves of electromagnetic waves applied to the body surface of the subject, or based on change in dielectric constant in the vicinity of the body surface when electromagnetic waves are applied to the body surface.

Displacement on the body surface caused by breathing is minute, and hence it is affected by a respiratory harmonic component relatively significantly. Displacement on the body surface around the chest is also affected by breathing. Therefore, when using a method of detecting heartbeats based on displacement on the body surface around the chest, the respiratory harmonic component interferes relatively significantly with cardiac signals. The invention can be applied to such a method to remove the respiratory harmonic component to improve the detection characteristics dramatically.

Removal of the respiratory harmonic component is effective not only for heartbeat detection based on body surface displacement but also for a method of detecting heartbeats based on which movement in body tissues by unit of electromagnetic waves passing through the body. Variation in body tissues caused by heartbeats (typically, strokes of the heart) is greater than displacement on the body surface caused by heartbeats, and hence the effect of respiratory harmonics becomes relatively small. Still, removal of the respiratory harmonics can improve the heartbeat detection characteristics.

In the invention, the cutoff frequencies of the low-pass filter and high-pass filter (first and second predetermined frequencies) can be set to be lower than a cardiac fundamental frequency and higher than a respiratory fundamental frequency. The cutoff frequencies of these filters may be the same or may be different within a range satisfying the aforementioned conditions.

In the invention, the cutoff frequency (first predetermined frequency) of the low-pass filter may be lower than the cardiac fundamental frequency and higher than the respiratory fundamental frequency, whereas the cutoff frequency (second predetermined frequency) of the high-pass filter may be higher than the cardiac fundamental frequency. In this case, the cutoff frequency is preferably lower than the second cardiac harmonics or third cardiac harmonics so that the second or third cardiac harmonics pass through. When using such high-pass filter, heartbeats of the subject are detected by focusing on the higher harmonic component of the cardiac signal. The higher harmonic noise removal unit then removes a respiratory harmonic component which interferes with the higher harmonic component of the cardiac signal. Filter characteristics of the high-pass filter may be such that the cardiac fundamental frequency is left to some extent as long as at least the respiratory fundamental frequency is cut off. Therefore, this configuration relaxes the requirements for the high-pass filter and enables use of simple and low-cost high-pass filter.

It is preferred in the invention that the cardiac signal processing apparatus further has a unit for acquiring an extraneous vibration signal relating to extraneous vibration applied to the body surface of the subject during measurement of the cardiac signal, and a unit for removing the extraneous vibration signal from the cardiac signal, and that the extraneous vibration signal is removed from the cardiac signal before the cardiac signal is input to the low-pass filter or high-pass filter.

The extraneous vibration corresponds to vibration in a place where the subject is present (for example, vibration in a vehicle), or vibration of the air caused by music or sound noise. By preliminarily removing noise caused by such vibration from the cardiac signal, more accurate heartbeat detection characteristics can be obtained.

The invention can be comprehended as a cardiac signal processing apparatus including at least part of the measures described above, or as a cardiac signal processing method including at least some of the processing steps described above. Further, the invention can be comprehended as a computer program stored in a non-transitory computer-readable medium. The program, when executed by a computer, causes the computer to execute the aforementioned method. The invention can be constituted by combining the aforementioned measures and processing steps as much as possible.

According to the invention, desirable heartbeat detection characteristics can be obtained by removing noise from a cardiac signal.

DESCRIPTION OF THE EMBODIMENTS

<First Embodiment>

A heartbeat detection system according to an embodiment of the invention will be schematically described. The heartbeat detection system according to this embodiment is a heartbeat detection system designed to detect a heartbeat of a subject to be measured with use of microwaves. This system is also applicable to subjects such as animals other than human beings. While the system is capable of detecting anything other than a heartbeat as long as it is of an organ working in the body, the following description of the embodiment will be described on the assumption that a heartbeat of a human body is the subject to be measured.

(System Configuration)

Figure 1:
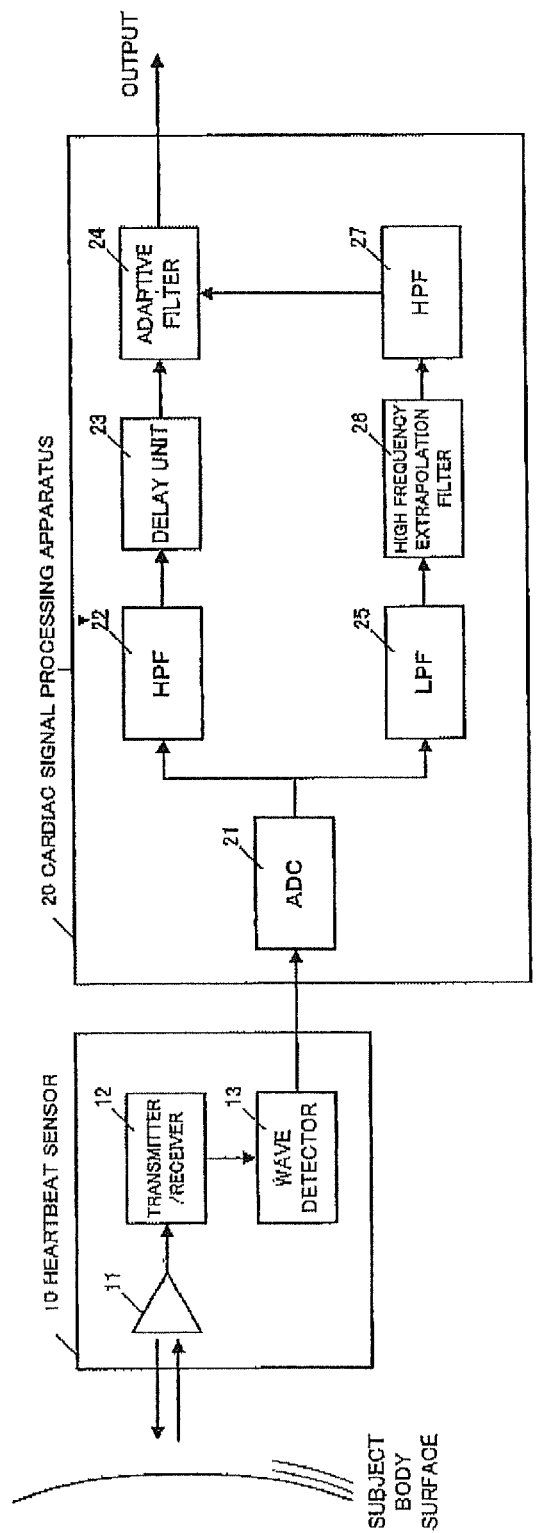
FIG. 1 is a diagram showing a functional configuration of a heartbeat detection system according to a first embodiment of the invention.

FIG. 1 is a diagram showing a functional configuration of a heartbeat detection system according to this embodiment. Schematically, the heartbeat detection system is composed of a heartbeat sensor 10 and a cardiac signal processing apparatus 20. While in this embodiment, the cardiac signal processing apparatus 20 forms the heartbeat detection system in combination with the heartbeat sensor 10, the cardiac signal processing apparatus 20 need not necessarily be provided integrally with the heartbeat sensor 10. The cardiac signal processing apparatus 20 may be provided separately from the heartbeat sensor 10, so that a cardiac signal is externally received and this received cardiac signal is subjected to signal processing.

The heartbeat sensor 10 has an antenna 11, a transmitter/receiver 12, and a wave detector 13. In this embodiment, 10 GHz microwaves are applied to the body surface of a subject from the transmitter/receiver 12 via the antenna 11, reflected waves from the body surface are received by the transmitter/receiver 12, and the received waves are detected by the wave detector 13.

The antenna 11 is unit for applying microwaves to the body surface of a subject and receiving the reflected waves therefrom. The antenna 11 is arranged, for example, to apply microwaves to the chest of the subject. When the heartbeat sensor is arranged on a seat, the antenna 11 is preferably arranged on its backrest so that microwaves are applied to the back side of the chest. However, microwaves may be applied to the front side of the chest.

The transmitter/receiver 12 is unit for transmitting microwaves to a subject, receiving reflected waves, and amplifying or frequency-converting the received reflected waves.

The wave detector 13 is unit for detecting the received reflected waves. The wave detector 13 detects microwaves by envelope detection (amplitude detection) or phase detection.

The cardiac signal processing apparatus 20 includes an AD converter (ADC) 21, a high-pass filter (HPF) 22, a delay unit 23, an adaptive filter 24, a low-pass filter (LPF) 25, a high frequency extrapolation filter 26, and a high-pass filter 27.

The cardiac signal processing apparatus 20 has an interface (not shown) for acquiring output (a cardiac signal) of the heartbeat sensor 10. The ADC 21 digitizes an analog cardiac signal acquired from the heartbeat sensor 10. The ADC 21 is not necessary when a digital signal can be acquired from the heartbeat sensor 10.

Figure 2A:
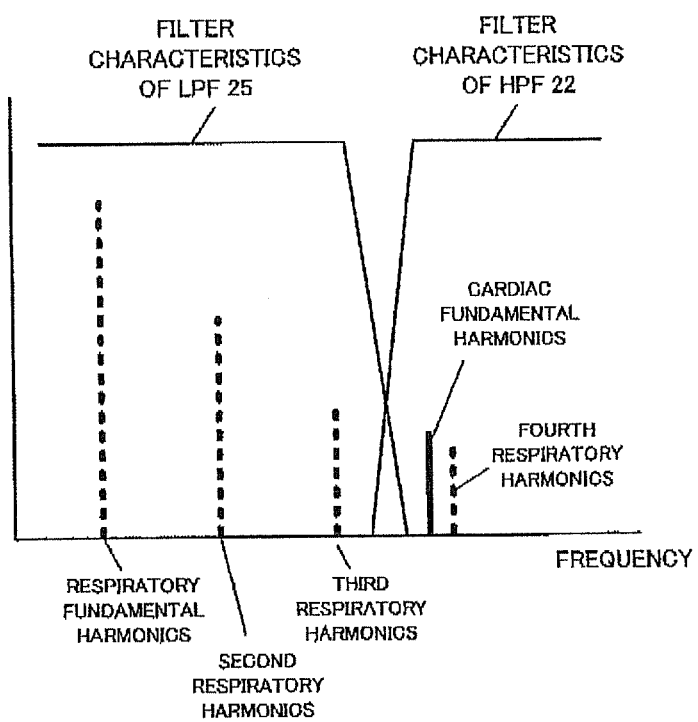
FIGS. 2A and 2B show diagrams of filter characteristics of a high-pass filter and a low-pass filter.

The signal digitized by the ADC 21 is sent to the LPF 25 by which the cardiac signal is removed and a respiratory signal (fundamental harmonics) is extracted. The normal heart rate is 60 to 180 beats per minute, that is, about 1 to 3 Hz, while the breathing rate is 10 to 20 breaths per minute, that is, about 0.15 to 0.3 Hz. Accordingly, the fundamental harmonics of the respiratory signal can be extracted from the cardiac signal by employing, as the LPF 25, a LPF which has a frequency between these values as a cutoff frequency. Since the respiratory signal is subjected to high frequency extrapolation processing as described later, the cutoff frequency of the LPF 25 is preferably determined such that a filtered signal contains not only fundamental harmonics of the respiratory signal but also several higher harmonics. FIG. 2A shows an example of filter characteristics of the LPF 25. In this example, the cutoff frequency of the LPF 25 is set to a frequency between a respiratory highest harmonics among frequencies lower than a fundamental frequency of a cardiac signal (a third harmonics in the shown example) and the fundamental frequency of the cardiac signal.

Since the higher harmonic component is removed from the respiratory signal by the LPF 25, the high frequency extrapolation filter 26 performs high frequency extrapolation processing to maintain a harmonic structure of the respiratory signal that is a quasi-periodic signal, so that a higher harmonic component of the respiratory signal is generated. Since this high frequency extrapolation processing is a well-known technique, detailed description thereof will be omitted here. Basically, the high frequency extrapolation processing is realized by copying an intermediate component of the respiratory signal (a higher harmonic component of the respiratory signal with a frequency equal to or lower than the cutoff frequency of the LPF 25) to a high frequency portion (equal to or higher than the cutoff frequency of the LPF 25) by unit of amplitude modulation. During this processing, the level of the high frequency portion is adjusted based on an envelope of frequency spectrum of the input respiratory signal.

After the respiratory harmonic component has been extrapolated by the high frequency extrapolation filter 26, the signal is input to the HPF 27, by which the higher harmonic component of the respiratory signal is extracted. As described later, the higher harmonic component of the respiratory signal is a component that is removed from a cardiac signal by the HPF 22. Therefore, the cutoff frequency of the HPF 27 is preferably the same or higher than the cutoff frequency of the HPF 22.

The cardiac signal digitized by the ADC 21 is input to the HPF 22, by which a respiratory signal is removed and a cardiac signal is extracted. In this embodiment, the cutoff frequency of the HPF 22 is the same as the cutoff frequency of the LPF 25 as shown in FIG. 2A. However, it may be different from the cutoff frequency of the LPF 25, as long as it is higher than a frequency that can separate a respiratory signal (fundamental harmonics) and a cardiac signal from an input signal, that is, a respiratory fundamental frequency, and lower than a cardiac fundamental frequency.

Figure 2B:
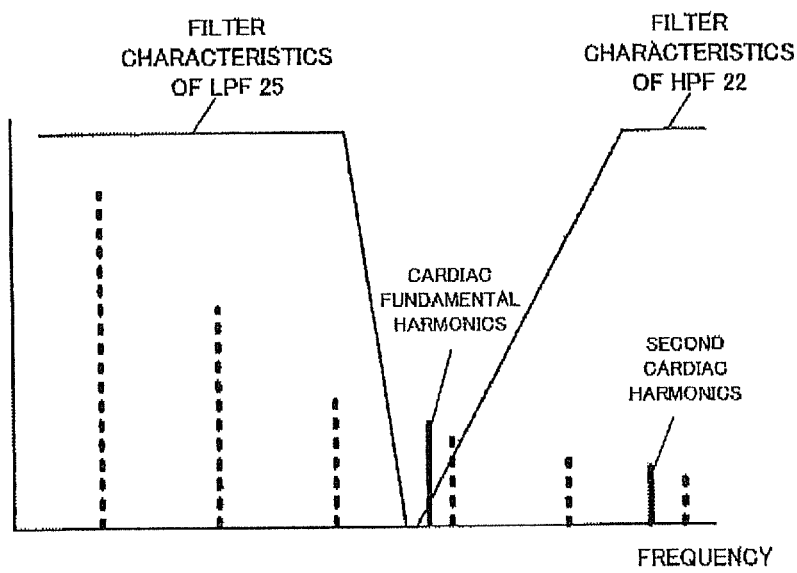

For example, the cutoff frequency of the HPF 22 can be a frequency higher than the fundamental frequency of a cardiac signal. Filter characteristics of the HPF 22 in this case are shown in FIG. 2B. Filter characteristics of the LPF 25 are the same as described above. In this example, it is intended to extract second higher harmonics of a cardiac signal. Thus, when a heartbeat is detected based on the second higher harmonics of a cardiac signal, requirements for the HPF 22 can be relaxed and hence a low-cost HPF can be used as the HPF 22.

The delay unit 23 compensates delay of the respiratory signal with respect to the cardiac signal. This corrects a time difference between the cardiac signal and the respiratory signal input to the adaptive filter 24.

The adaptive filter 24 is a filter for removing a respiratory harmonic component generated by high frequency extrapolation from a cardiac signal. The adaptive filter 24 is a filter employing an adaptive algorithm for realizing removal of a reference signal, which is a known technique. Therefore, detailed description thereof will be omitted. Basically, the adaptive filter 24 is a filter which self-adjusts its filter factor so as to minimize a difference (error signal) between a reference signal and a result obtained by filtering an input signal (prediction signal). When a signal having the same amplitude and phase as the respiratory harmonic component in an input signal can be complemented by the high frequency extrapolation filter, the respiratory harmonics may be removed from the cardiac signal by adding a respiratory harmonic signal after reversing the phase thereof, without using the adaptive filter.

The heartbeat detection system according to this embodiment makes it possible to remove a respiratory harmonic component interfering with a cardiac signal. This reduces signal distortion caused by interference of respiratory harmonics and hence makes it possible to obtain desirable heartbeat detection characteristics.

<Second Embodiment>

A heartbeat detection system according to this embodiment is assumed to be used in a vehicle. In a vehicle, vibration is given to the body of a subject due to effects of sound noise, vibration of the vehicle or the like. When used in such an environment, the heartbeat detection system is required to be able to suppress the effect of extraneous vibration.

Figure 3:
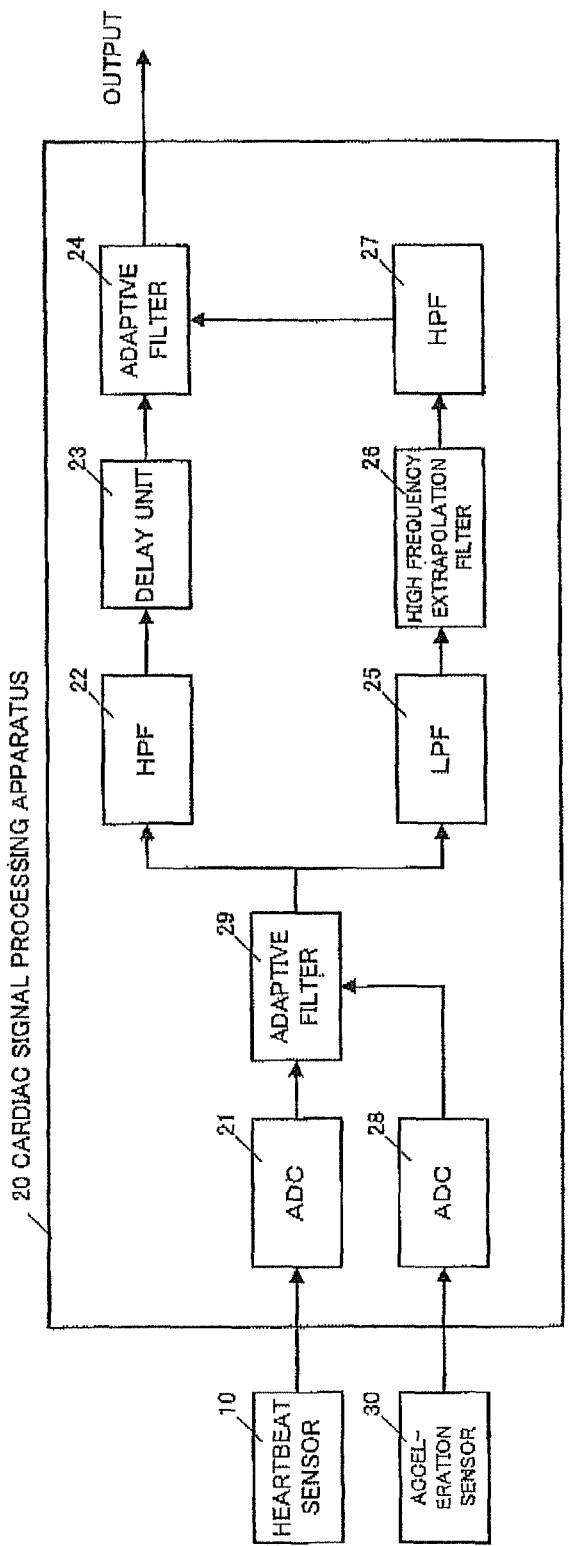
FIG. 3 is a diagram showing a functional configuration of a heartbeat detection system according to a second embodiment.

FIG. 3 is a diagram showing a functional configuration of a heartbeat detection system according to this embodiment. In this embodiment, the heartbeat detection system is composed of a heartbeat sensor 10, an acceleration sensor 30, and a cardiac signal processing apparatus 20. Since the heartbeat sensor 10 is the same as that of the first embodiment, description thereof will be omitted here.

The acceleration sensor 30 is, for example, fixedly arranged in a vehicle to acquire an acceleration signal applied to the vehicle. Based on the acceleration applied to the vehicle, vibration applied to the subject can be obtained. The acceleration sensor 30 may be, for example, a MEMS (Micro Electro Mechanical System) type acceleration sensor. Further, the method of detecting acceleration may be any one, such as electrostatic capacity detection method, piezoresistance method, or thermal detection method.

The cardiac signal processing apparatus 20 also uses a signal from the acceleration sensor 30 as an input. An AD converter 28 digitizes an analog vibration signal obtained from the acceleration sensor 30. An adaptive filter 29 uses a vibration signal that is output from the acceleration sensor 30 as a reference signal to remove a signal having a high correlation with the reference signal from the cardiac signal output from the heartbeat sensor 10. Like the adaptive filter 26, the adaptive filter 29 is a filter for removing noise, and has the same configuration as that of the adaptive filter 26. Therefore, detailed configuration thereof will be omitted.

Processing after the removal of the vibration signal from the cardiac signal is the same as in the first embodiment. Specifically, the cardiac signal is divided into a low-frequency signal and a high-frequency signal, respiratory harmonics are generated from the low-frequency signal, and respiratory harmonics are removed from the high-frequency signal.

In this manner, effects of extraneous vibration or the like applied to the vehicle, that is, effects of noise not generated by the body are removed before the processing for removing interference by the respiratory harmonics, whereby it is made possible to prevent generation of interference waves caused by harmonic regeneration of an external signal having a frequency component lower than that of the cardiac signal. This improves the effect of suppressing interference waves to the heartbeats, and hence improves the heartbeat detection characteristics.

The vibration signal to be removed by the adaptive filter 29 is not limited to the signal obtained from the acceleration sensor. Ambient noise or music played back in the vehicle can also constitute noise to a cardiac signal. Therefore, it is also preferable to remove a detection signal of a sound collector (microphone) or an output signal from sound equipment.

<Possible Modification>

Although the embodiments have been described on the assumption that the heartbeat detection system includes both a heartbeat sensor and a cardiac signal processing apparatus which are arranged in a vehicle or the like, the heartbeat sensor and the cardiac signal processing apparatus can be installed separately in different places. For example, it is conceivable that a cardiac signal acquired by the heartbeat sensor is transmitted to the cardiac signal processing apparatus installed in a separate place via a network so that the signal is processed thereby.

Although in the description above, the object to be processed is a cardiac signal that is obtained from the heartbeat sensor which receives reflected waves generated by applying microwaves to the back of a subject, the object to be processed may be any cardiac signal obtained by an arbitrary detection method as long as the cardiac signal is interfered by respiratory harmonics. In general, any cardiac signal obtained based on body surface displacement of the chest or displacement in the body (e.g. variation in size of an organ) of the subject is interfered by a respiratory harmonic component. Accordingly, the respiratory harmonic component can be removed desirably by applying the signal processing technique according to the invention to a cardiac signal obtained based on body surface displacement of the chest or displacement in the body of the subject.

Further, although the description above has been made in terms of an example in which various filters or the like are each formed by a specific circuit or DSP (digital signal processor), the cardiac signal processing apparatus may be realized by a computer including a CPU, a RAM, and a ROM so that various types of signal processing are performed by the CPU executing a program stored in a non-transitory computer-readable medium.

What is claimed is:

1. A cardiac signal processing apparatus comprising:
    a cardiac signal acquisition unit configured to acquire cardiac signals relating to heartbeats of a subject;
    a low-pass filter configured to allow passage of those cardiac signals having a first predetermined frequency or lower, among the cardiac signals;
    a higher harmonic noise acquisition unit configured to acquire harmonic signals of low-frequency noise by performing high frequency extrapolation on the signals output from the low-pass filter unit;
    a high-pass filter configured to allow passage of those cardiac signals having a second predetermined frequency or higher, among the cardiac signals; and
    a higher harmonic noise removal unit configured to remove the harmonic signals of low-frequency noise from the signals output from the high-pass filter.

2. The cardiac signal processing apparatus according to claim 1, wherein the cardiac signal is a signal obtained by measurement based on displacement on a body surface around the chest or displacement in the body of the subject.

3. The cardiac signal processing apparatus according to claim 1, wherein the first and second predetermined frequencies are lower than a cardiac fundamental frequency and higher than a respiratory fundamental frequency.

4. The cardiac signal processing apparatus according to claim 1, wherein:
    the first predetermined frequency is lower than a cardiac fundamental frequency and higher than a respiratory fundamental frequency; and
    the second predetermined frequency is higher than the cardiac fundamental frequency.

5. The cardiac signal processing apparatus according to claim 1, wherein the higher harmonic noise removal unit is an adaptive filter which uses the harmonic signal of low-frequency noise as a reference signal.

6. The cardiac signal processing apparatus according to claim 1, further comprising:
    a sensor configured to acquire an extraneous vibration signal relating to extraneous vibration applied to a body surface of the subject during measurement of the cardiac signal; and
    a unit for removing the extraneous vibration signal from the cardiac signal,
    wherein the cardiac signal from which the extraneous vibration signal has been removed is input to the low-pass filter and the high-pass filter.

7. A cardiac signal processing method comprising:
    a cardiac signal acquisition step of acquiring cardiac signals relating to heartbeats of a subject;
    a low-pass filtering step of allowing passage of those cardiac signals having a first predetermined frequency or lower, among the cardiac signals;
    a higher harmonic noise acquisition step of acquiring harmonic signals of low-frequency noise by performing high frequency extrapolation on the signals output in the low-pass filtering step;
    a high-pass filtering step of allowing passage of those cardiac signals having a second predetermined frequency or higher, among the cardiac signals; and
    a higher harmonic noise removal step of removing the harmonic signals of low-frequency noise from the signals output in the high-pass filtering step.

* * * * *